United States Patent

Wootton et al.

[11] 4,237,131
[45] Dec. 2, 1980

[54] PROSTAGLANDIN ANALOGUES

[75] Inventors: Gordon Wootton, Sawbridgeworth; Richard W. Moore, Harlow, both of England

[73] Assignee: Beecham Group Limited, Great Britain

[21] Appl. No.: 48,516

[22] Filed: Jun. 14, 1979

[30] Foreign Application Priority Data

Jun. 15, 1978 [GB] United Kingdom ............... 27017/78

[51] Int. Cl.³ .................. C07D 413/06; A61K 31/415
[52] U.S. Cl. .......................... 424/248.51; 424/248.54; 424/250; 424/267; 424/273 R; 548/301; 548/313; 548/312; 548/309; 544/139; 544/370; 546/210
[58] Field of Search ............... 548/313, 301, 309, 312; 546/210; 544/139, 370; 424/273 R, 267, 248.51, 248.54, 250

[56] References Cited

U.S. PATENT DOCUMENTS 4,147,796  4/1979  Wooton ............... 548/313

Primary Examiner—Henry R. Jiles
Assistant Examiner—Robert T. Bond
Attorney, Agent, or Firm—Jacobs & Jacobs

[57] ABSTRACT

A compound of the formula (I):

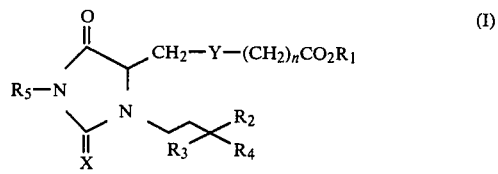

wherein:
X is O or S;
Y is $-CH_2-CH_2-$, $-CH=CH-$ or $-C\equiv C-$;
n is 1 to 5;
$R_1$ is hydrogen or $CO_2R_1$ represents an ester group in which the $R_1$ moiety contains from 1 to 12 carbon atoms;
$R_2$ is hydrogen or $C_{1-4}$ alkyl;
$R_3$ is hydroxy or protected hydroxy;
$R_4$ is $C_{1-9}$ alkyl, $C_{3-8}$ cycloalkyl or $C_{3-8}$ cycloalkyl-$C_{1-6}$ alkyl; or
$R_2$ and $R_4$ taken with the carbon atom to which they are joined represent a $C_{5-8}$ cycloalkyl group; and
$R_5$ is $(CH_2)_aNR_6R_7$, wherein a is 0 to 3 and $R_6$ and $R_7$ are hydrogen, $C_{1-4}$ alkyl or phenyl $C_{1-4}$ alkyl, or $R_6$ and $R_7$ taken with the nitrogen atom to which they are joined represent a 4 to 7 membered heterocyclic ring which may contain as sole further hetero atom one oxygen atom or one optionally $C_{1-4}$ alkyl substituted nitrogen atom; allyl or propargyl; $(CH_2)_b-CO-(CH_2)_c-CH_3$ wherein b+c is 1 to 5 and b is not zero; or S-$R_8$ wherein $R_8$ is $C_{1-6}$ alkyl, phenyl, or phenyl substituted by a halogen, trifluoromethyl, $C_{1-6}$ alkyl, $C_{1-6}$ alkoxy or nitro group; and salts thereof has useful pharmaceutical activity including bronchodilator activity.

32 Claims, No Drawings

PROSTAGLANDIN ANALOGUES

This invention relates to novel compounds having pharmacological activity, to a process for their preparation, to intermediates useful in that process and to pharmaceutical compositions containing them.

German Offenlegungsschrift No. 2,724,948 discloses that compounds of the general formula (A):

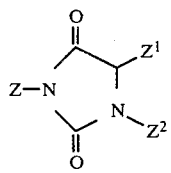

wherein

Z is hydrogen or alkyl; one of $Z^1$ and $Z^2$ is a group $-CH_2-X-X^1-X^2$ in which X is phenylene, $-C\equiv C-$, cis-, or trans- $-CH=CH-$ or $-CH_2-CQ_2-$, where each radical Q independently of the other is hydrogen or alkyl or the two radicals Q together are $C_{4-6}$ alkylene, $X^1$ is a covalent bond or a straight or branched $C_{1-6}$ alkylene chain, in which one methylene group is optionally substituted by an oxa ($-O-$) group, with the proviso that at least one carbon atom separates the oxa group from a $-C\equiv C$, $-CH=CH-$ or CO group, and $X^2$ is tetrazolyl, carboxyl, carboxamide, hydroxymethylene or alkoxycarbonyl;

and the other one of $Z^1$ and $Z^2$ is a group $-Y-Y^1-Y^2-Y^3$ in which Y is $-CR_2-CH_2-$, where each radical R independently of the other is hydrogen or methyl, $Y^1$ is carbonyl, methylene, methylene substituted by a hydroxy group or methylene substituted by a hydroxy and an alkyl group, $Y^2$ is a covalent bond or straight-chain or branched $C_{1-7}$ alkylene optionally substituted on the carbon atom adjacent to $Y^1$ by one or two mutually independent alkyl, bicycloalkyl or cycloalkyl groups, $Y^3$ is hydrogen, hydroxy, $C_{1-7}$ (preferably $C_{1-4}$) alkoxy, cycloalkyl, bicycloalkyl, phenyl, benzyl, phenoxy or benzyloxy, where each phenyl, benzyl, phenoxy or benzyloxy by one or more hydroxy, halogen, nitro, amino, acylamino, alkenyl, alkoxy, phenyl and/or alkyl groups, which themselves may be substituted by one or more halogens or Y is a bond, $-CH_2-$ or $-CH_2.CH_2-$; and $Y^1$, $Y^2$ and $Y^3$ together are cycloalkyl which is substituted by a hydroxy group which is preferably separated by 3 carbon atoms from the hydantoin ring, have similar pharmacological activity to natural prostaglandins.

We have now discovered a class of compounds which have useful pharmacological activity and which are structurally distinct from the compounds disclosed in Offenlegungsschrift No. 2,724,948.

This class of compounds of this invention is also structurally distinct from the compounds of formula (B):

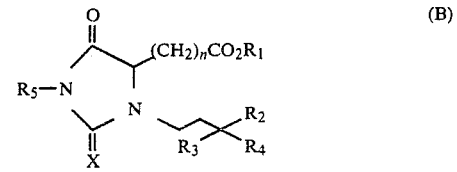

wherein:
X is O to S;
n is 1 to 8;
$R_1$ is hydrogen, or $CO_2R_1$ represents an ester group in which the $R_1$ moiety contains from 1–12 carbon atoms;
$R_2$ is hydrogen, $C_{1-4}$ alkyl, or phenyl;
$R_3$ is hydroxy or protected hydroxy;
$R_4$ is hydrogen, $C_{1-9}$ alkyl, $C_{3-8}$ cycloalkyl, $C_{3-8}$ cycloalkyl -$C_{1-6}$ alkyl, phenyl, phenyl $C_{1-6}$ alkyl, naphthyl, naphthyl-$C_{1-6}$-alkyl, any of which phenyl or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or
$R_2$ and $R_4$ taken with the carbon atom to which they are joined represent a $C_{5-8}$ cycloalkyl group;
$R_5$ is hydrogen, $C_{1-6}$ alkyl, $C_{1-6}$ alkyl substituted by a nitro, hydroxy, $C_{1-6}$ alkoxy, $CO_2A$, $(CO_2A)_2$, CN or halogen group, $C_{5-8}$ cycloalkyl, phenyl, phenyl-$C_{1-6}$ alkyl, phenyl-$C_{3-6}$ cycloalkyl, any of which phenyl moieties may be substituted by one or more halogen, trifluorormethyl, $C_{1-6}$ alkyl, $C_{1-6}$ alkoxy or nitro groups; or a group $CO_2A$; in $R_5$ when present A is hydrogen or $CO_2A$ represents an ester group in which the A moiety contains from 1 to 12 carbon atoms; and salts thereof; which are disclosed in our West German Offenlegungsschrift No. 2,755,771 as having useful prostaglandin-like activity. It should be noted that West German Offenlegungsscrift No. 2,755,771 published after the date of filing of the priority application for this invention.

Accordingly, the present invention provides a compound of formula (I):

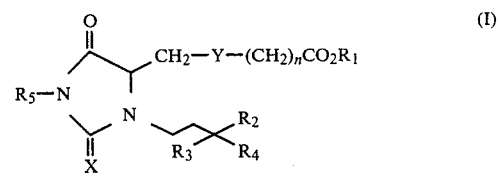

wherein:
X is O or S;
Y is $-CH_2-CH_2-$, $-CH=CH-$ or $-C\equiv C-$;
n is 1 to 5;
$R_1$ is hydrogen or $CO_2R_1$ represents an ester group in which the $R_1$ moiety contains from 1 to 12 carbon atoms;
$R_2$ is hydrogen or $C_{1-4}$ alkyl;
$R_3$ is hydroxy or protected hydroxy;
$R_4$ is $C_{1-9}$ alkyl, $C_{3-8}$ cycloalkyl or $C_{3-8}$ cycloalkyl-$C_{1-6}$ alkyl; or
$R_2$ and $R_4$ taken with the carbon atom to which they are joined represent a $C_{5-8}$ cycloalkyl group; and
$R_5$ is $(CH_2)_aNR_6R_7$, wherein a is 0 to 3 and $R_6$ and $R_7$ are hydrogen, $C_{1-4}$ alkyl or phenyl $C_{1-4}$ alkyl, or $R_6$ and $R_7$ taken with the nitrogen atom to which they are joined represent a 4 to 7 membered heterocyclic ring which may contain as sole further hetero atom one oxygen atom or one optionally $C_{1-4}$ alkyl substituted nitrogen atom; allyl or propargyl; $(CH_2)_b$—CO—$(CH_2)_c$—$CH_3$ wherein b+c is 1 to 5 and b is not zero; or S-$R_8$ wherein $R_8$ is $C_{1-6}$ alkyl, phenyl, or phenyl substituted by a halogen, trifluoromethyl, $C_{1-6}$ alkyl, $C_{1-6}$ alkoxy or nitro group; and salts thereof.

One group of such compounds is as defined but wherein $R_5$ is $(CH_2)_aNR_6R_7$, wherein a is 0 to 3 and $R_6$ and $R_7$ are hydrogen or $C_{1-4}$ alkyl, or $R_6$ and $R_7$ taken with the nitrogen atom to which they are joined represent a 4 to 7 membered heterocyclic ring containing one hetero atom; allyl or propargyl; $(CH_2)_b$—CO—$(CH_2)_c$—$CH_3$ wherein b+c is 1 to 5 and b is not zero; or S-$R_8$ wherein $R_8$ is $C_{1-6}$ alkyl, phenyl, or phenyl substituted by a halogen, trifluoromethyl, $C_{1-6}$ alkyl, $C_{1-6}$ alkoxy or nitro group; and salts thereof.

More suitably X is O. Also, most suitably Y is —$CH_2$—$CH_2$—. Often n will be 2 to 4, for example 3.

Suitable examples of $R_1$ include hydrogen, methyl, ethyl, n- and iso- propyl, n-,sec- and tert butyl, phenyl, benzyl, tolyl and the like, while normally hydrogen or $C_{1-6}$ alkyl groups are preferred.

Suitable examples of $R_2$ include hydrogen, methyl and ethyl. More suitably $R_2$ is hydrogen or methyl, preferably methyl.

Suitable protected hydroxyl groups $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl groups or like groups. Preferably $R_3$ is hydroxyl.

Suitable groups $R_4$ when $R_4$ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, $R_4$ may be a group $CH_2R_9$, $CH(CH_3)R_9$ or $C(CH_3)_2R_9$, wherein $R_9$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups $CH(CH_3)R_9$ and $C(CH_3)_2R_9$ wherein $R_9$ is straight chain butyl, pentyl and hexyl.

Other suitable examples of $R_4$ when $R_4$ is an alkyl group include the lower alkyl groups, that is when $R_4$ is a $C_{1-4}$ alkyl group.

When $R_4$ is or contains a $C_{3-8}$ cycloalkyl moiety, the moiety may be cyclopropyl. The moiety may also be a $C_{5-8}$ cycloalkyl moiety such as a cyclohexyl moiety. Examples of suitable $C_{1-6}$ alkyl moieties when $R_4$ is a $C_{3-8}$ cycloalkyl -$C_{1-6}$ alkyl group include methyl, ethyl, propyl, butyl and pentyl.

Also, $R_2$ and $R_4$ taken with the carbon atom to which they are joined can represent a $C_{5-8}$ cycloalkyl group, such as the cyclohexyl group.

When $R_5$ is a group $(CH_2)_aNR_6R_7$, it may with advantage be amino. However, other suitable examples of $R_5$ include the group wherein $R_6$ and $R_7$ are methyl, ethyl and n- and iso- propyl, and the group wherein $NR_6R_7$ represent the ring

a Is suitably 0 to 1, but when $R_6$ and $R_7$ represent a ring, then a is preferably 1.

Other examples of uncyclised $R_6$ and $R_7$ in a group $R_5$ of formula $(CH_2)_aNR_6R_7$ include benzyl and phenylethyl. Often in such groups $R_6$ and $R_7$ will be identical, for example dibenzyl.

Other examples of cyclised $R_6$ and $R_7$ in a group $R_5$ of formula $(CH_2)_aNR_6R_7$ include morpholino and

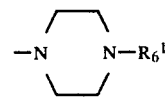

wherein $R_6{}^l$ is hydrogen or $C_{1-4}$ alkyl, such as methyl. In general it will be appreciated from the foregoing that when $R_6$ and $R_7$ are in cyclised form the corresponding ring preferably contains 6 ring atoms.

Thus it can be seen that suitable examples of $R_5$ include when $R_5$ is $(CH_2)_aNR_6R_7$, wherein a is 0, 1 or 2, and $R_6$ and $R_7$ are hydrogen, methyl or benzyl, or $R_6$ and $R_7$ taken with the nitrogen atom to which they are joined represent a 5 or 6 membered hetrocyclic ring which may contain as sole further hetero atom one oxygen atom, or one optionally $C_{1-4}$ alkyl substituted nitrogen atom.

Preferred such examples include those wherein a is 0 or 1, $R_6$ and $R_7$ are hydrogen or methyl, or $R_6$ and $R_7$ taken with the nitrogen atom to which they are joined represent pyrrolidino, morpholino or piperidino.

Most preferably such $R_5$ groups are amino, or a is 1 and $R_6$ and $R_7$ are hydrogen or methyl.

$R_5$ may also be a group $(CH_2)_b$—CO—$(CH_2)_c$—$CH_3$ as defined. Suitably b is 1 and c is 0 or 1, preferably b is 1 and c is 0.

When $R_5$ is a group S-$R_8$, then suitably examples of $R_8$ include methyl, ethyl, n- and iso- propyl; phenyl; or phenyl substituted by one or two of the substituents previously defined.

The compounds of the formula (I) may form conventional salts. Such salts include those with alkali and alkaline earth metals, suitably sodium and potassium, and ammonium and substituted ammonium salts.

From the aforesaid it will be seen that one particularly suitably group of compounds within formula (I) is of formula (II):

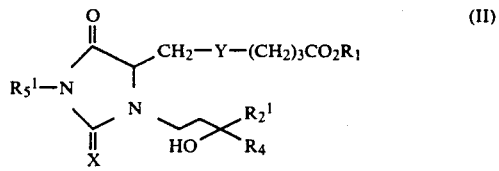

wherein
X, Y, $R_1$ and $R_4$ are as defined;
$R^1{}_2$ is hydrogen, methyl or ethyl; and
$R^1{}_5$ is $(CH_2)_aNR_6R_7$ as defined; and salts thereof.
In formula (II) suitably X is O.
In formula (II) suitably X is O.

$R^1{}_5$ is more suitably hydrogen or methyl, preferably methyl.

When $R_4$ is a $C_{1-9}$ alkyl group, it is normally a $C_{4-9}$ alkyl group. In such cases suitable and preferred straight chain and branched groups $R_4$ include those previously described. Such preferred groups $R_4$ include straight chain pentyl, hexyl, and heptyl and of these normally the most useful is straight chain hexyl. Other preferred groups $R_4$ include $CH(CH_3)R_9$ and $C(CH_3)_2R_9$ wherein $R_9$ is straight chain butyl, pentyl or hexyl.

In formula (II) $R_4$ may also suitably be a group of formula (III):

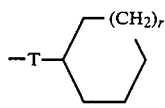
(III)

wherein T is a bond, or a $C_{1-6}$ alkylene group which may be straight chain or branched by one or two methyl groups at the same or different carbon atoms; and r is 0 to 3. In formula (III) often T will be a group $-(CH_2)_q-$ wherein q is 0 to 4. Also suitably r is 1.

Suitable and preferred examples of $R^1{}_5$ in formula (II) include those groups said to be suitable and preferred for such $R_5$ groups hereinbefore.

A second interesting group of compounds within formula (I) are of formula (IV):

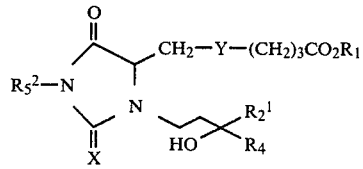
(IV)

wherein the variable groups, and suitable and preferred examples thereof, are as for formula (II); and $R^2{}_5$ is allyl or propargyl; and salts thereof.

A third particularly useful group of compounds within formula (I) is of formula (V):

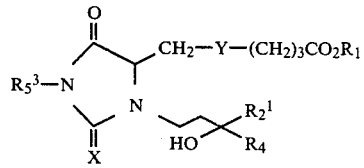
(V)

wherein the variable groups, and suitable and preferred examples thereof, are as formula (II); and $R^3{}_5$ is a group $(CH_2)_b-CO-(CH_2)_c-CH_3$ as previously defined; and salts thereof.

Suitable examples of $R^3{}_5$ include $CH_2COCH_3$ and the other groups hereinbefore described as suitable for such $R_5$ groups.

A fourth group of compounds within formula (I) is of formula (VI):

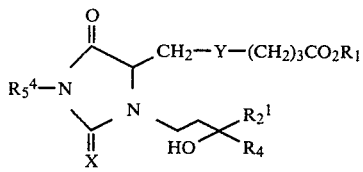
(VI)

wherein the variable groups, and suitable and preferred examples thereof, are as for formula (II); and $R^4{}_5$ is a group $S-R_8$ as defined; and salts thereof.

Suitable examples of $R^4{}_5$ include groups hereinbefore described as suitable for such $R_5$ groups.

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the normal methods.

The present invention further provides a process for the preparation of the compounds of the formula (I), wherein $R_5$ is not $(CH_2)_aNR_6R_7$, which process comprises the cyclisation of a compound of formula (VII):

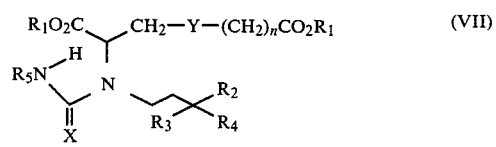
(VII)

wherein the variable groups are as defined; and thereafter if desired or necessary converting Y, $R_1$ or $R_3$ in the thus formed compound into other variables Y, $R_1$ or $R_3$.

The compound of the formula (VII) is conveniently prepared in situ during the reaction of a compound of the formula (VIII):

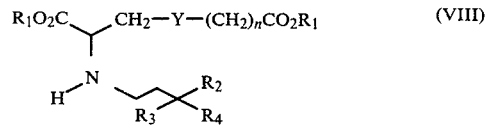
(VIII)

wherein n, $R_1$, $R_2$, $R_3$ and $R_4$ are as defined, with $R_5NCX$, a preferred process of the invention for compounds of formula (I) wherein $R_5$ is other than amino.

This preferred process is suitably carried out under reflux in an inert solvent such as benzene or the like. It should be stated that when in this reaction $R_5$ is a sterically hindered group then this reaction may proceed only as far as the uncyclised compound of formula (VII) in which case the necessary cyclisation of the compound (VII) can be achieved with a strong base, such as sodium hydride or sodium ethoxide, in a dry organic solvent. Sodium ethoxide in benzene, or potassium t-butoxide in toluene, benzene or hexamethylphosphoramide are suitable reagents.

The present invention also provides a further process for the preparation of compounds of the formula(I) wherein $R_5$ is not $(CH_2)_aNR_6R_7$ in which a is 0 or 1, which process comprises the reaction of a compound of the formula (IX):

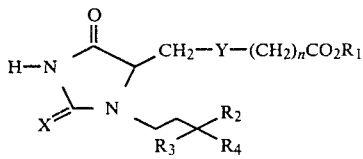

(IX)

wherein the variables are as defined in formula (I), with $R_5L$ wherein $R_5$ is as defined in formula (I) and L is a good leaving group. In such reactions it may be necessary to convert the compound of the formula (VII) first to an alkali metal salt at the 10-position (prostaglandin numbering).

This reaction is carried out under conventional conditions for substitution reactions. L may suitably be a halide.

It will be appreciated that in any such reaction including a free amino group in $R_5$ then it may be necessary or advisable to protect this free amino group during the reaction.

Compounds of the formula (IX) may be prepared by the reaction of a compound of formula (VIII) as defined with a salt $M^+C^-NX$, wherein $M^+$ is a metal ion, in the presence of acid.

In this reaction the necessary acid may conveniently be provided by using an acid addition salt of the compound of formula (VIII), such as the hydrochloride, or by carrying out the reaction in aqueous acid.

The subsequent conversion of a compound of the formula (I) to another compound of the formula (I) wherein Y, $R_1$ or $R_3$ are altered, when desired or necessary, may be achieved in conventional manner.

For example, if desired, compounds wherein Y is $-C\equiv C-$ may be reduced to compounds wherein Y is $-CH=CH-$ in known manner. Suitably this reaction is carried out using catalytic hydrogenation, such as Lindlar catalysis.

When Y is $-CH=CH-$, it may be reduced to $-CH_2-CH_2$ in known manner, suitably using catalytic hydrogenation such as transition metal catalysis.

Also, if desired the group $R_1$ in the compound may be varied by conventional esterification and/or de-esterification reactions. Similarly, protected $R_3$ hydroxy moieties may be deprotected in conventional manner. For example when $R_3$ is a benzyloxy group, the benzyl group may readily be removed by acidic hydrolysis. Thus it may be seen that 'protected hydroxy' compounds of the formula (I) are useful intermediates in the preparation of the corresponding 'free hydroxy' compounds of the formula (I).

Also when a compound of the formula (I) contains an acidic hydrogen atom, a salt thereof may be prepared in conventional manner for example by reacting the compound of the formula (I) with the required base.

Compounds of the formula (I) wherein $R_5$ is $NR_6R_7$ may be prepared by the N-amination of a compound of formula (IX) as hereinbefore defined.

Suitably this reaction is carried out with reagents such as O-(2,4-dinitrophenyl) hydroxylamine.

Compounds of the formula (I) wherein $R_5$ is $CH_2NR_6R_7$ may be prepared by a coupling reaction between the amine $HNR_6R_7$ and a compound of the formula (IX). Suitably this reaction is carried out as for Mannich type reactions, for example by use of formaldehyde as the coupling reagent.

After these reactions any desired or necessary interconversion of groups in the resultant compound of the formula (I) may be carried out as hereinbefore described.

The compounds of formula (VIII) are known compounds or may be prepared in analogous manner to known compounds.

Compounds within the formula (I) have particularly useful pharmacological activity. For example compounds within the formula (I) have anti-gastric secretion activity, anti-ulcer activity, cardiovascular activity e.g. anti-hypertensive activity, platelet aggregation inhibition activity, affect the respiratory tract, e.g. bronchodilator activity, and have anti-fertility, smooth muscle and anti-arrhythmic activity.

Compounds of the formula (I) may accordingly be used in the treatment and prophylaxis of corresponding disorders in humans and animals.

In general it may be said that compounds within the formula (I) have a range of pharmacological activities similar to those shown by the natural prostaglandins, but that these activities tend to be rather more selective.

The compounds of the formula (I) are especially useful as bronchodilation agents.

The invention therefore also provides a pharmaceutical composition comprising a compound of the formula (I) ans a pharmaceutically acceptable carrier.

The compounds of the formula (I) also have good stability.

Clearly the formulation of the said pharmaceutical composition will depend on the nature of the activity shown by the chosen compound of the formula (I), and on factors such as a preference in a particular area of therapy for a particular mode of administration.

The composition may be in the form of tablets, capsules, powders, granules, lozenges or liquid preparations, such as oral or sterile parenteral solutions or suspension.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in pharmaceutical practice. Oral liquid preparations may be in the form of, for example, aqueous or oily suspensions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilising the compound of the formula (I) and a sterile vehicle. The compound, depending on the vehicle and concentration used, can be either suspended or dissolved in the vehicle. In preparing solutions the compound can be dissolved for injection and filter sterilised before filling into a suitable vial or ampoule and sealing. Advantageously, adjuvants such as local anaesthetic, preservatives and buffering agents can be dissolved in the vehicle. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human being or animals which comprises the administration to the sufferer of an effective amount of a compound of the formula (I). Normally however the compounds will be used in the therapy of human disorders.

The following Examples illustrate the preparation of compounds of the formula (I) and their pharmacological properties.

EXAMPLE OF PREPARATION OF INTERMEDIATES

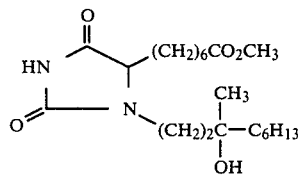

Dry hydrogen chloride gas was passed into an ice-cold solution of dimethyl 2-[N-(3'-hydroxy-3'-methyl)n-nonyl] aminoazelate (40 g) in dry ether (1 l). The ether was evaporated in vacuo and the resulting hydrochloride was stirred with water (300 ml). A solution of potassium cyanate (8.2 g; 1.01 eq) in water (20 ml) was added and the resulting suspension was stirred at room temperature for 1.5 hours then at reflux for 1.5 hours. The mixture was allowed to cool and the product was extracted into dichloromethane. The dichloromethane solution was washed with brine until the washings were neutral then was dried and evaporated to give a yellow gum (38 g). A sample was purified via column chromatography (silica gel: 30:1) using chloroform, and chloroform methanol mixtures as eluants to give 1-(3'-hydroxy-3'-methyl-n-nonyl)-5-(6''-methoxycarbonyl-n-hexyl) hydantoin as a pale yellow gum.

I.R. (cm$^{-1}$): 3500, [OH];

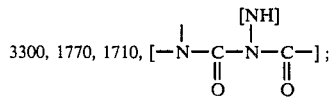

1730, [CO$_2$CH$_3$].

NMR ($\gamma$): 7.85, (m), [—C$\underline{H}_2$CO$_2$CH$_3$]; 7.5 to 6.5, (m), [—N—C$\underline{H}_2$]; 6.4, (s), [—CO$_2$C$\underline{H}_3$]; 5.95, (broad s), [—N—C$\underline{H}$].

Mass Spec: C$_{21}$H$_{36}$N$_2$O$_4$ (m*—H$_2$O), requires: 380.2675, found: 380.2659,

EXAMPLE 1

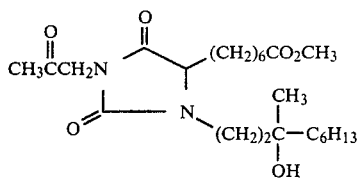

Compound 1

1-(3'-Hydroxy-3'-methyl-n-nonyl)-5-(6''-methoxycarbonyl-n-hexyl) hydantoin (5 g) in dry dimethylformamide (10 mls) was added to a stirred suspension of sodium hydride (0.38 g; 80% oil dispersion) in dry dimethylformamide (20 ml), under nitrogen, at room temperature. The mixture was stirred overnight. Bromoacetone (1.72 g) in dry dimethylformamide (10 ml) was added dropwise and the mixture was stirred for 24 hours at room temperature. The product was partitioned between very dilute hydrochloric acid and ether. The ether solution was washed with 5% aqueous sodium hydroxide solution, and with brine until the washings were neutral, then was dried and evaporated in vacuo to give a dark yellow oil. The oil was chromatographed on silica gel (30:1) using chloroform, 1% methanol/chloroform and 2% methanol/chloroform as eluants to give 1-(3-hydroxy-3'-methyl-n-nonyl)-3-acetoxymethyl-5-(6''-methoxycarbonyl-n-hexyl) hydantoin (2.2 g) as a pale yellow oil.

Analysis: C$_{24}$H$_{41}$N$_2$O$_6$, requires: C, 63.41; H, 9.31; N, 6.16%, found: C, 63.32; H, 9.61; N, 6.40%.

The compound in table 1 was produced in a similar manner.

TABLE 1

| | | |
|---|---|---|
| Compound no. | R$_5$X | R$_5$ |
| 2 | CH$_2$=CHCH$_2$Br | CH$_2$=CH—CH$_2$ |

EXAMPLE 2

Preparation of 1-(3'-Hydroxy-3'-methyl-n-nonyl)-3-amino-5-(6'-methoxycarbonyl-n-hexyl) hydantoin

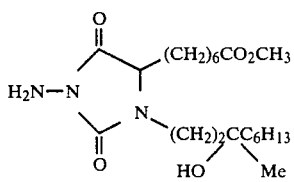

COMPOUND 3

1-(3'-Hydroxy-3'-methyl-n-nonyl)-5-(6''-methoxycarbonyl-n-hexyl)hydantoin (2 g, 0.005 mole) in dry dimethylformamide (10 ml) was added to a stirred suspension of sodium hydride (0.165 g, 0.0055 mole, 80% dispersion in oil) under nitrogen at room temperature. The mixture was stirred for 3 hours.

O-(2,4-dinitrophenyl)-hydroxylamine (prepared as described by T. Sheradsky, J. Heterocyclic. Chem. 4, 413 (1967), (1 g, 0.005 mole) was added portion-wise and the mixture was stirred for 3 hours at room temperature. The dark orange reaction mixture was poured into water (100 ml) and extracted with ether (2×100 ml). The combined organic solutions were washed with brine (4×100 ml), dried (Na$_2$SO$_4$) and evaporated in vacuo to give a dark brown oil (1.6 g). The oil was chromatographed on silica gel (Merck Kieselgel 60; 100 g) using 1% methanol/chloroform as eluant to give 1-(3'-hydroxy-3'-methyl-n-nonyl)-3-amino-5-(6''-methoxycarbonyl-n-hexyl)hydantoin (0.7 g) as an orange gum.

IR (cm$^{-1}$) 3450 [OH] 3350, 3200 [N—NH$_2$]

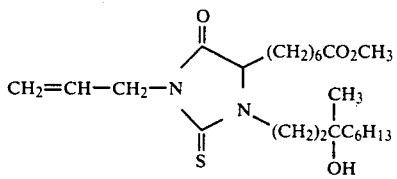

1760, 1720 (broad) [—N—C—N—C—; CO$_2$Me]

NMR ($\tau$) 7.8 (br S, 1H, OH) CDCl$_3$ 7.7 (t, 2H, C$\underline{H}_2$ CO$_2$ Me), approx. 7 to 6 (br m, 2H, N—CH$_2$), 6.3 (s, 3H, CO$_2$ Me), 5.95 (t, 1H, N—CH), 5.85 (br, S, 2H, H$_2$H—N), Mass spectrum C$_{21}$H$_{37}$N$_3$O$_4$ [M*—H$_2$O], Requires: 395.2784, Found: 395.2760.

EXAMPLE 3

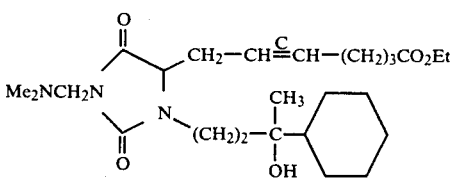

COMPOUND 4

Dimethyl 2-[N-(3'-hydroxy-3'-methyl-n-nonyl)] amino azelate (25 g) was refluxed with allyl isothiocyanate (6.41 g) in dry toluene (100 mls) for 3 hours. The toluene was evaporated in vacuo to leave a yellow oil (35.1 g) which was distilled via short-path distillation to give 1-(3'-hydroxy-3'-methyl-n-nonyl)-3-(prop-2''-enyl)-5-(6'''-methoxycarbonyl-n-hexyl)-2-thiohydantoin as a pale yellow gum (18.2 g).

B pt 183° at 1 mb

EXAMPLE 4

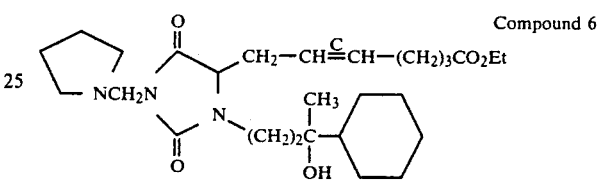

Compound 5

To 1-(3'-hydroxy-3'-cyclohexyl-butyl)-5-(6''-ethoxycarbonyl-n-hex-2''-enyl) hydantoin (2.0 g, 5.5 m mol) in methanol (8 ml) at 0° C. (ice-bath) was added dimethylamine (25% solution in water) (2ml, 11 m mol) and formalin (40%) (0.5 ml, 7 m mol). The solution was stirred for two hours at 0° C., and the solvent removed under reduced pressure. Dry benzene (15 ml) was added and removed under reduced pressure. This procedure was repeated twice. The product (a deep yellow oil) was chromatographed on neutral alumina (a one inch thick pad) using chloroform as eluant to give 1-(3'-hydroxy-3'-cyclohexyl-butyl)-3-(dimethylaminomethyl)-5-(6''-ethoxycarbonyl-N-hex-2''-enyl) Hydantoin (1.8 g, 75%) as a yellow oil.

I.R. ($\nu_{max}$) cm$^{-1}$ 1765 and

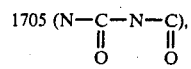

1705 (N—C—N—C), with C=O groups 1730 (CO$_2$Et)

N.M.R. ($\tau$) 4.5 (m. 2H, vinyl protons), 5.65 (2H, s, N—CH$_2$—N), 5.86 (2H, q, OC$\underline{H}_2$, Me), 7.70 (6H, s, NMe$_2$), 8.75 (3H, t, OCH$_2$—C$\underline{\underline{H}}_3$), 8.86 (3H, s,

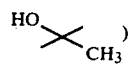

H.R.M.S. m/e 465.3201, C$_{25}$H$_{43}$N$_3$O$_5$ requires 465.3203.

Similarly prepared were the compounds of Examples 5 to 9.

EXAMPLE 5

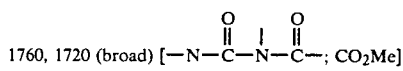

Compound 6

1-(3'-hydroxy-3'-cyclohexyl-butyl)-3-(pyrrolidinomethyl)-5-(6''-ethoxycarbonyl-n-hex-2''-enyl) hydantoin from 1-(3'-hydroxy-3'-cyclohexyl-butyl)-5-(6''-ethoxycarbonyl-n-hex-2''-enyl) hydantoin, pyrrolidine and formalin in 68% yield.

I.R. ($\nu_{max}$) cm$^{-1}$ 1765 and

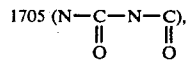

1705 (N—C—N—C), 1730 (CO$_2$Et)

N.M.R. ($\tau$) 4.55 (m, 2H, vinyl protons), 5.50 (2H, s, N—CH$_2$—N), 5.86 (2H, q, OC$\underline{H}_2$Me), 8.75 (3H, t, OCH$_2$—M$\underline{\underline{e}}$) 8.87 (3H, s,

H.R.M.S. m/e 491.3359, C$_{27}$H$_{45}$N$_3$O$_5$ requires 491.3355.

EXAMPLE 6

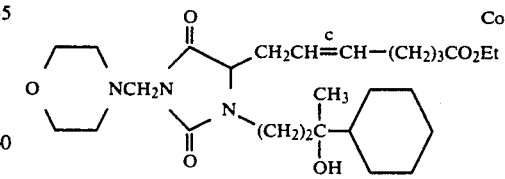

Compound 7

1-(3'-hydroxy-3'-cyclohexyl-butyl)-3-(morpholinomethyl)-5-(6''-ethoxycarbonyl-n-hex-2''-enyl) hydantoin from 1-(3'-hydroxy-3'-cyclohexyl-butyl)-5-(6''-ethoxycarbonyl-n-hex-2''-enyl) hydantoin, morpholine and formalin 65% yield.

I.R. ($\nu_{max}$) cm$^{-1}$ 1765 and

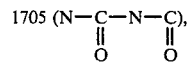
1735 (CO₂Et)

N.M.R. (τ) 4.55 (2H, s, vinyl protons), 5.40 (2H, s, N—CH₂—N), 5.87 (2H, q, OCH₂Me), 6.30 (4H, m, —CH₂—O—CH₂—), 8.75 (3H, t, OCH₂—Me), 8.87 (3H, s,

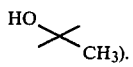

H.R.M.S. 507.3275, $C_{27}H_{45}N_3O_6$ requires 507.3308.

EXAMPLE 7

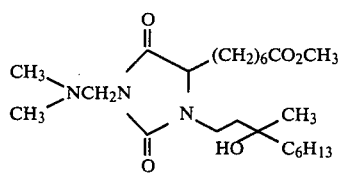

1-(3'-hydroxy-3'-methyl-n-nonyl)-3-dimethylaminomethyl-5-(6''-methoxycarbonyl-n-hexyl) hydantoin (compound 8) was prepared from 1-(3'-hydroxy-3'-methyl-n-nonyl)-5-(6''-methoxycarbonyl-n-hexyl) hydantoin, formaldehyde and dimethylamine.

EXAMPLE 8

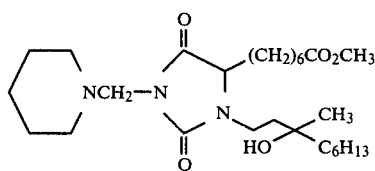

1-(3'-hydroxy-3'-methyl-n-nonyl)-3-piperidinomethyl-5-(6''-methoxycarbonyl-n-hexyl) hydantoin (compound 9) was prepared from 1-(3'-hydroxy-3'-methyl-n-nonyl)-5-(6''-methoxycarbonyl-n-hexyl) hydantoin, formaldehyde and piperidine.

EXAMPLE 9

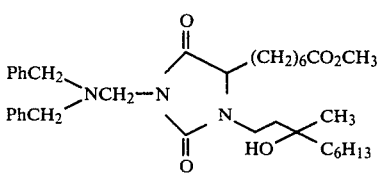

1-(3'-hydroxy-3'-methyl-n-nonyl)-3-dibenzylaminomethyl-5-(6''-methoxycarbonyl-n-hexyl) hydantoin (compound 10) was prepared from 1-(3'-hydroxy-3'-methyl-n-nonyl)-5-(6''-methoxycarbonyl-n-hexyl) hydantoin, formaldehyde and dibenzylamine.

EXAMPLE 10

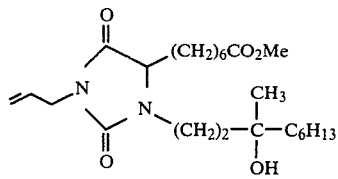

To a stirred slurry of sodium hydride (80% dispersion in oil) (0.164 g, 5.5 m mol) in dry dimethylformamide (20 ml) was added 1-(3'-hydroxy-3'-methyl-n-nonyl)-5-(6''-methoxycarbonyl-n-hexyl) hydantoin (2.19 g, 5.5 m mol) in dry dimethylformamide (20 ml) under nitrogen at room temperature. The solution was stirred overnight at room temperature. Allyl bromide (0.665 g, 5.5 m mol) in dry dimethylformamide (5 ml) was added and the solution stirred at room temperature for a further twenty four hours. Ether (200 ml) was added, and the solution washed successively with 0.05 M hydrochloric acid, 10% sodium hydroxide solution and brine until neutral. The solution was dried over sodium sulphate, the solvent removed under reduced pressure and the product (2.02 g) chromatographed on silica gel (60 g) using chloroform as eluant to give 1-(3'-hydroxy-3'-methyl-n-nonyl)-3-allyl-5-(6''-methoxycarbonyl-N-hexyl) hydantoin (1.5 g, 62 m mol) as a colourless oil.

I.R. ($\nu_{max}$) cm⁻¹ 3450 (OH), 1765,

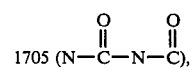

1735

N.M.R. (τ) 4.2–5.0 (3H, m, —CH=CH₂), 5.96 (3H, m N—CH₂—CH,

6.36 (3H, s, CO₂Me), 7.25 (1H, b, OH removed with D₂O).

H.R.M.S. m/e 438.3093, $C_{24}H_{42}N_2O_5$ requires 438.3091.

ANALYSIS: $C_{24}H_{42}N_2O_5$ required C, 65.72, H, 9.65, N, 6.39. Found: C, 65.92, H, 9.95, N, 6.20.

EXAMPLE 11

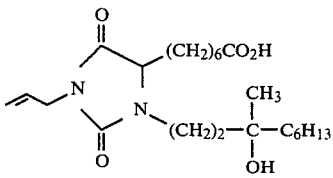

1-(3'-hydroxy-3'-methyl-n-nonyl)-3-allyl-5-(6''-methoxycarbonyl-n-hexyl) hydantoin (1.0 g, 2.3 m mol) in methanol (20 ml), was reluxed overnight with 10% aqueous potassium carbonate (10 ml). The mixture was cooled, and ice (10 g) added. The solution was acidified to pH 1 with concentrated hydrochloric acid and extracted with ether (3×100 ml). The combined ether extracts were extracted with 5% sodium bicarbonate solution (3×100 ml). The combined bicarbonate layers were washed with ether (50 ml), acidified to pH 1.5 with concentrated hydrochloric acid and extracted with ether (3×100 ml). The combined ether layers were washed with saturated brine (3×50 ml) and dried over sodium sulphate. Removal of the solvent under reduced pressure gave 1-(3'-hydroxy-3'-methyl-n-nonyl)-3-allyl-5-(6''-carboxy-n-hexyl) hydantoin (0.6 g, 69%).

I.R. ($\nu_{max}$) cm$^{-1}$ 3500–2550 (OH, CO$_2$H), 1765, 1700

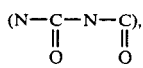

1700 (CO$_2$H)

N.M.R. ($\tau$) 3.55 (2H, b, OH, CO$_2$H), 4.2–5.0 (3H, m, vinyl group), 5.93 (3H, m, N-$\underline{CH_2}$-vinyl,

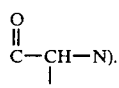

H.R.M.S. m/e 424.2945, C$_{23}$H$_{40}$N$_2$O$_5$ requires 424.2933.

PHARMOCOLOGICAL DATA

Bronchodilator Activity (a) The Compounds were examined for their ability to inhibit 5-hydroxytryptamine induced bronchoconstriction in the anaesthetised, artifically respired guinea-pig (Konzett-Rossler preparation).

Compound 1 had an ED$_{50}$ of 445 μg/kg i.v.
Compound 3 had an ED$_{50}$ of 1 μg/kg i.v.

(b) The Compounds were also examined for their ability to protect conscious guinea pigs against bronchoconstriction induced by an histamine aerosol (Herxheimer test). The Compounds were administered by aerosol.

The results obtained are shown in the Table 1.

The aerosol was produced in the following manner.

Water soluble Compounds were dissolved in normal saline at a concentration of 1 mg/ml. Water insoluble Compounds were dissolved in ethanol at a concentration of 10 mg/ml. These solutions were then diluted to the test concentration with normal saline.

TABLE 1

| Compound | % Increase in pre-convulsive coughing time |
|---|---|
| 5 | 100% at 10 μg/ml after 2 min |
| 6 | 116% at 10 μg/ml after 2 min |
| 7 | 88% at 10 μg/ml after 2 min |
| 8 | 109% at 10 μg/ml after 2 min |

Toxicity

No toxic effects were observed in any of these tests.

FURTHER CHARACTERISING DATA

Compound 8

I.R. (cm$^{-1}$) film: 3450 (OH); 1770,

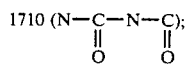

1740 (CO$_2$CH$_3$)

N.M.R. ($\tau$ CCl$_4$): 7.85, s, 1H, (OH); 7.75, s, 6H, (N(CH$_3$)$_2$); 6.5, brm, 2H, (NCH$_2$); 6.35, s, 3H, (CO$_2$CH$_3$); 6.0, m, 1H, (NCH); 5.7, s, 2H, (NCH$_2$N).

Mass Spec: C$_{24}$H$_{45}$N$_3$O$_5$ (M*) requires: 455.3358; found: 455.3365.

Compound 9

I.R. (cm$^{-1}$) film: 3450 (OH); 1765,

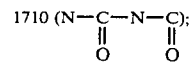

1740 (CO$_2$CH$_3$)

N.M.R. ($\tau$ CCl$_4$): 7.75, t, 2H, (CH$_2$CO$_2$CH$_3$); 7.5, m, 4H, (CH$_2$NCH$_2$); 7.3, s, 1H, (O$\underline{H}$); 6.5, brm, 2H, (NCH$_2$); 6.35, s, 3H, (CO$_2$CH$_3$); 6.0, m, 1H, (NCH); 5.15, s, 2H, (NCH$_2$N).

Mass Spec: C$_{27}$H$_{49}$N$_3$O$_5$ (M*) requires: 495.3671; found: 495.3641.

What we claim is:

1. A compound selected from the group consisting of a hydantoin of the formula:

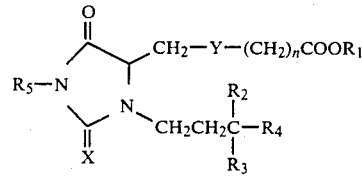

wherein

X is O or S;
Y is —CH$_2$CH$_2$—, —CH=CH— or —C≡C—;
n has a value of from 1 to 5 inclusively;
R$_1$ is hydrogen, alkyl of 1 to 6 carbon atoms, phenyl, benzyl or tolyl;
R$_2$ is hydrogen or alkyl of 1 to 4 carbon atoms;
R$_3$ is hydroxy, alkanoyloxy of 1 to 4 carbon atoms or benzyloxy;
R$_4$ is alkyl of 1 to 9 carbon atoms, cycloalkyl of 3 to 8 carbon atoms, or alkyl of 1 to 6 carbon atoms substituted with cycloalkyl of 5 to 8 carbon atoms; and
R$_5$ is
(i)

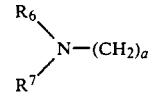

in which a has a value of from 0 to 3 inclusively and each of R$_6$ and R$_7$ taken independently of the other is hydrogen, alkyl of 1 to 4 carbon atoms or phenylalkyl of 7 to 10 carbon atoms or R$_6$ and R$_7$ taken together, together with the nitrogen atom to which they are joined are pyrrolidino, piperidino, morpholino or 4-alkylpiperazino wherein alkyl has from 1 to 4 carbon atoms;
(ii) allyl or propargyl;
(iii)

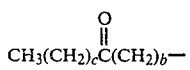

in which c+b has a value of from 1 to 5 and b is at least 1; or (iv) $R_8$—S— in which $R_8$ is alkyl of 1 to 6 carbon atoms, unsubstituted phenyl or phenyl substituted with halo, trifluoromethyl, alkyl of 1 to 6 carbon atoms, alkoxy of 1 to 6 carbon atoms or nitro, and the alkali metal, alkaline earth metal, ammonium and substituted ammonium salts thereof when $R_1$ is hydrogen.

2. A compound according to claim 1 wherein X is O.
3. A compound according to claim 1 wherein Y is —CH$_2$—CH$_2$—.
4. A compound according to claim 1 wherein n is 2 to 4.
5. A compound according to claim 4 wherein n is 3.
6. A compound according to claim 1 wherein $R_1$ is hydrogen.
7. A compound according to claim 1 wherein $R_1$ is alkyl of 1 to 6 carbon atoms.
8. A compound according to claim 1 wherein $R_2$ is hydrogen or methyl.
9. A compound according to claim 1 wherein $R_3$ is hydroxy.
10. A compound according to claim 1 wherein $R_4$ is alkyl of 4 to 9 carbon atoms.
11. A compound according to claim 10 wherein $R_4$ is n-pentyl, n-hexyl or n-heptyl.
12. A compound according to claim 11, wherein $R_4$ is n-hexyl.
13. A compound according to claim 1 wherein $R_4$ is hex-2-yl, hept-2-yl or oct-2-yl.
14. A compound according to claim 1 wherein $R_4$ is alkyl of 1 to 6 carbon atoms substituted with cyclohexyl.
15. A compound according to claim 1 wherein $R_4$ is cyclohexyl.
16. A compound according to claim 1 wherein $R_5$ is

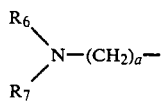

wherein
a has a value of 0, 1 or 2;
each of $R_6$ and $R_7$ taken independently of the other is hydrogen, methyl or benzyl or $R_6$ and $R_7$ taken together, together with the nitrogen atom to which they are joined are pyrrolidino, piperidino, morpholino or 4-alkylpiperizino wherein alkyl has from 1 to 4 carbon atoms.

17. A compound according to claim 16 wherein a is 0 or 1, each of $R_6$ and $R_7$ independently of the other is hydrogen or methyl, or $R_6$ and $R_7$ taken together, together are pyrrolidino, morpholino or piperidino.

18. A compound according to claim 17 wherein a is 0 and each of $R_6$ and $R_7$ is hydrogen.
19. A compound according to claim 17 wherein a is 1 and each of $R_6$ and $R_7$ taken independently of the other is hydrogen or methyl.
20. A compound according to claim 1 wherein $R_5$ is allyl or propargyl.
21. A compound according to claim 1 wherein $R_5$ is

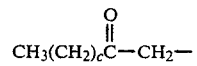

in which c has a value of 0 or 1.

22. A compound according to claim 1 wherein $R_5$ is $R_8$-S-.
23. A compound according to claim 1 wherein said hydantoin has the formula:

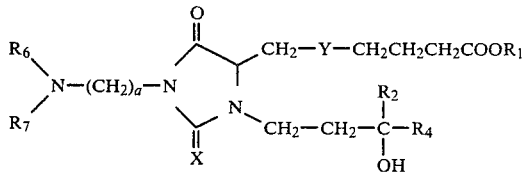

wherein
$R_1$, $R_4$, $R_6$, $R_7$, X, Y and a are as therein defined; and
$R_2$ is hydrogen, methyl or ethyl.

24. A compound according to claim 23 wherein a has a value of 0, 1 or 2, and each of $R_6$ and $R_7$ taken independently of the other is hydrogen, methyl or benzyl, or $R_6$ and $R_7$ taken together, together with the hydrogen atom to which they are joined are pyrrolidino, piperidino, morpholino or 4-alkylpiperazino wherein alkyl contains from 1 to 4 carbon atoms.

25. A compound according to claim 24, wherein a is 0 or 1, each of $R_6$ and $R_7$ taken independently of the other is hydrogen or methyl, or $R_6$ and $R_7$ taken together, together with the nitrogen atom to which they are joined, are pyrrolidino, morpholino or piperidino.

26. A compound according to claim 25 wherein a is 0 and each of $R_6$ and $R_7$ is hydrogen.
27. A compound according to claim 25 wherein a is 1 and each of $R_6$ and $R_7$ is hydrogen or methyl.
28. A compound according to claim 23 wherein $R_4$ is n-pentyl, n-hexyl or n-heptyl.
29. A compound according to claim 28 wherein $R_4$ is n-hexyl.
30. A compound according to claim 23 wherein $R_4$ is cyclohexyl.
31. A pharmaceutical composition for effecting a prostaglandin-like effect comprising an effective amount of a compound according to claim 1 in combination with a pharmaceutically acceptable carrier.
32. A method for the treatment of humans or animals of conditions responsive to natural prostaglandins, which comprises administering to to a human or animal in need thereof an effective amount of a compound according to claim 1.

* * * * *